(12) United States Patent
Perruna et al.

(10) Patent No.: US 8,758,783 B1
(45) Date of Patent: Jun. 24, 2014

(54) WATER-IN-OIL EMULSION COMPRISING PIGMENTS IN THE WATER PHASE

(71) Applicant: L'Oreal, Paris (FR)

(72) Inventors: Gisela M. Perruna, Rahway, NJ (US); Ashini Amin, Monroe, NJ (US)

(73) Assignee: L'Oreal, Paris (FR)

( * ) Notice: Subject to any disclaimer, the term of this patent is extended or adjusted under 35 U.S.C. 154(b) by 19 days.

(21) Appl. No.: 13/721,835

(22) Filed: Dec. 20, 2012

(51) Int. Cl.
*A61K 9/107* (2006.01)

(52) U.S. Cl.
USPC .............................. 424/401; 424/63; 424/61

(58) Field of Classification Search
None
See application file for complete search history.

(56) References Cited

U.S. PATENT DOCUMENTS

| | | | |
|---|---|---|---|
| 5,055,500 A * | 10/1991 | Peters et al. | 523/319 |
| 2003/0216327 A1 | 11/2003 | Rubinstenn et al. | |
| 2004/0137023 A1 | 7/2004 | Dalko et al. | |
| 2007/0015840 A1 | 1/2007 | Dalko et al. | |
| 2010/0189804 A1 | 7/2010 | Schlossman et al. | |
| 2011/0195103 A1 | 8/2011 | Perez Arcas et al. | |
| 2011/0243869 A1 | 10/2011 | Brijlall et al. | |
| 2011/0305735 A1 | 12/2011 | Cebrian Puche et al. | |
| 2012/0128777 A1 | 5/2012 | Keck et al. | |

FOREIGN PATENT DOCUMENTS

| | | |
|---|---|---|
| EP | 1366743 A1 | 12/2003 |
| WO | WO-2006067327 A2 | 6/2006 |
| WO | WO-2012072245 A2 | 6/2012 |
| WO | WO-2012112796 A2 | 8/2012 |

* cited by examiner

*Primary Examiner* — Anand Desai
*Assistant Examiner* — Melissa Mercier
(74) *Attorney, Agent, or Firm* — Novak Druce Connolly Bove + Quigg LLP

(57) ABSTRACT

Provided is a composition and especially a cosmetic composition comprising: A) an oily phase and B) an aqueous phase which comprises: a) water, b) a pigment, c) a modified phospholipid, and d) an alkyl substituted diol comprising 5 or more carbons; wherein the composition is in the form of an water-in-oil emulsion, and wherein the pigment essentially remains in the water phase. Also provide is a method of producing the composition which comprises: 1) obtaining a mixture of a modified phospholipid and an alkyl substituted diol comprising 5 or more carbons in the alkyl chain; 2) obtaining a mixture of water and a pigment; 3) combining the mixture of the modified phospholipids and the alkyl substituted diol with the mixture of the pigment and water; 4) obtaining an oil composition; and 5) combining the mixture from 3) with the oil composition of 4) to form an water-in-oil emulsion.

22 Claims, No Drawings

WATER-IN-OIL EMULSION COMPRISING PIGMENTS IN THE WATER PHASE

TECHNICAL FIELD

The present disclosure is concerned with water-in-oil emulsions that comprise pigments, wherein the pigments are in the water or inner phase of the emulsion, and a process for fabricating the emulsions. It has been found according to the present invention that a combination of a modified phospholipid along with an alkyl substituted diol having an alkyl chain of at least 5 carbon atoms makes it possible to essentially maintain pigments including untreated pigments in the water phase. The present disclosure is especially concerned with personal care products. The disclosure further relates to the use of the composition, in particular for treating, caring for, making up and/or cleaning the skin, superficial body growths (hair, eyelashes, nails) and/or mucous membranes. Also, compositions of the present disclosure are suitable for topical application, and in particular is a cosmetic and/or dermatological composition.

Additional advantages and other features of the present disclosure will be set forth in part in the description that follows and in part will become apparent to those having ordinary skill in the art upon examination of the following or may be learned from the practice of the present disclosure. The advantages of the present disclosure may be realized and obtained as particularly pointed out in the appended claims. As will be realized, the present disclosure is capable of other and different embodiments, and its several details are capable of modifications in various obvious respects, all without departing from the present disclosure. The description is to be regarded as illustrative in nature, and not as restrictive.

BACKGROUND ART

Pigments are important for various cosmetic applications, such as those for the face, eye, lip and nail. For instance, when used as part of facial foundations, pigments help to cover facial blemishes or blend uneven colors on the face. When used as part of facial powders, pigments provide coverage of complexion that is considered by the user as undesirable. When used as facial blushes, pigments enhance the cheeks with colors that are trendy or desirable.

The dispersion of pigments is an important aspect of personal care formulations. Pigments are typically delivered in one of two common types of emulsions: water-in-oil (W/O) emulsions or oil-in-water (O/W) emulsions in the presence of emulsifiers. The nature of the emulsifier is an important factor as to what type of emulsion that may be formed, and thus how the dispersion of the pigments will occur.

Regarding the type of emulsion to be formed, the Bancroft rule state that an emulsifier will promote dispersion of the phase in which it does not dissolve. Accordingly, when a pigment is combined with a lipophilic emulsifier (that is, hydrophobic), water is the dispersed phase while oil is the continuous phase, thus forming a W/O emulsion. When a pigment is combined with a lipophobic emulsifier (that is, hydrophilic), oil is the dispersed phase and water is the continuous phase, thus forming an O/W emulsion.

When present in an emulsion, pigments are commonly or typically included in the outer phase. In the case of water-in-oil emulsions, the pigments are typically located in the oil phase. Accordingly, a challenge facing the personal care industry is to provide an efficient formulation that would maintain pigments and especially untreated pigments in the water phase of a water-in-oil emulsion.

SUMMARY OF DISCLOSURE

The present disclosure addresses problems encountered in the prior art and provides water-in-oil emulsions whereby pigments essentially remain in the water phase. According to the present disclosure, migration of the pigments from the water phase into the oil phase is prevented or at least significantly avoided. Water-in-oil emulsions of the present disclosure comprise a composition comprising A) an oily phase and B) an aqueous phase that comprises a) water; b) at least one pigment; c) at least about 0.1% by weight based upon the weight of the composition of at least one modified phospholipid; d) at least about 0.1% by weight based upon the weight of the composition of at least one alkyl substituted diol comprising 5 or more carbons in the alkyl chain, and wherein the pigment essentially remains in the water phase.

Another aspect of the present disclosure is concerned with a method of producing the above disclosed composition which comprises:

1) obtaining a mixture of at least one modified phospholipid and at least one alkyl substituted diol comprising 5 or more carbons in the alkyl chain;
2) obtaining a mixture of water and at least one pigment;
3) combining the mixture of the at least one modified phospholipid and the at least one alkyl substituted diol with the mixture of water and the at least one pigment;
4) obtaining an oil composition; and
5) combining the mixture from 3) with the oil composition of 4) to form a water-in-water emulsion;

wherein the amount of the at least one modified phospholipid is at least about 0.1% by weight based upon the weight of the composition and the amount of the at least one alkyl substituted diol is at least about 0.1% by weight based upon the weight of the composition.

A still further aspect of the present disclosure relates to a process for the cosmetic treatment of a keratinous substance, which comprises applying the above disclosed composition to the keratinous substance.

As will be realized the disclosure is capable of other and different embodiments, and its several details are capable of modifications in various obvious respects, without departing from the disclosure. Accordingly, the description is to be regarded as illustrative in nature and not as restrictive.

DESCRIPTION OF BEST AND VARIOUS MODES FOR CARRYING OUT DISCLOSURE

The present disclosure is concerned with water-in-oil emulsions comprising at least one pigment in the water phase. According to the present disclose, the pigment is dispersed in and is stabilized in the water phase. In addition, the present disclosure makes it possible to address the problem whereby the shade of the composition dramatically changes due to the pigment not wetting properly. Accordingly, the present disclosure makes it possible to achieve a substantially consistent shade as the composition transitions from the wet to dry state. Furthermore, the present disclosure makes it possible to achieve enhanced color intensity.

The compositions of the present disclosure comprise: A) an oily phase and B) an aqueous phase, wherein the aqueous phase comprises: a) water, b) at least one pigment, c) at least one modified phospholipid, and d) at least one alkyl substituted diol comprising 5 or more carbons in the alkyl chain. The composition is in the form of a water-in-oil emulsion, and the pigment essentially remains (e.g. at least about 80% and more typically at least about 90%) in the water phase.

It has been found according to the present disclosure that the combination of the modified phospholipid and alkyl substituted diol comprising 5 or more carbons in the alkyl chain allows for relatively uniform pigment dispersion in the aqueous phase. The combination of at least one modified phospholipid and at least one alkyl substituted diol comprising 5 or more carbons in the alkyl chain provides adequate hydrophobicity and hydrophilicity that prevents the pigments from agglomeration in the water phase of the water-in-oil emulsion. It is believed that the hydrophobic part of the modified phospholipid will attach to the pigment. Similarly, the alkyl chain of the diol will also attach to the pigment. At the same time, the hydrophilic part of the modified phospholipid and hydroxyl groups of the alkyl substituted diol comprising 5 or more carbons in the alkyl chain will extend to the water phase of the water-in-oil emulsion.

Working together as a combination, the modified phospholipid and the alkyl substituted diol comprising 5 or more carbons in the alkyl chain prevent the particles of the pigments from agglomering with each other, and thus, the separated pigment particles remain suspended in the water phase of the water-in-oil emulsion. When either the modified phospholipid or the alkyl substituted diol comprising 5 or more carbons in the alkyl chain is not included in the composition, the pigment will not be properly dispersed. It has been observed that if only the alkyl substituted diol comprising 5 or more carbons in the alkyl chain is used, as shown by Comparison Example 1, the pigments would not be properly dispersed.

According to an embodiment of the invention, a modified phospholipid such as lecithin or hydrogenated lecithin is found to be particularly useful as the emulsifier for the water-in-oil (W/O) emulsion for the dispersion of the pigments. Lecithin is a glycerol molecule which has been derivatized with two fatty acids and one phosphatidylcholine chain. Often, one of the two fatty acids contains one double bond. According to an embodiment of the invention, the hydrogenated lecithin is Lecinol S-10 by Nikkol.

The amount of modified phospholipid is typically at least about 0.1%, more typically about 0.2 to about 0.6% by weight and even more typically about 0.2 to about 0.3% by weight based upon the total weight of the composition. The maximum amount of modified phospholipid according to certain embodiments is about 1% by weight based upon the weight of the composition.

The alkyl substituted diol employed according to the present disclosure has 5 or more carbons in the alkyl chain and more typically has 5 to 7 carbon atoms in the alkyl chain. The diol or glycol moiety of the alkyl substituted diol is typically ethylene glycol or propylene glycol with ethylene glycol being the more typical. Examples of alkyl substituted glycols having at least 5 carbon atoms in the alkyl chain include, but are not limited to: 1,2-heptanediol, 1,2-octanediol and 1,2-nonanediol. According to an embodiment of the present disclosure, caprylyl glycol (or 1,2-octanediol; Dermosoft® Octiol from Dr. Straetmans) is a preferred stabilizer.

The alkyl substituted diol is typically employed in an amount of at least about 0.1%, more typically in an amount of about 0.1 to about 0.3% and even more typically about 0.2 to about 0.3% by weight based upon the total weight of the composition. The maximum amount of alkyl substituted diol according to certain embodiments is about 1% by weight based upon the weight of the composition.

When the composition contains less than about 0.1% by weight of the modified phospholipid and less than about 0.1% of the alkyl substituted diol, the composition does not have satisfactory viscosity to achieve a stable water-in-oil emulsion as illustrated in Comparison Example 2.

The weight ratio of the modified phospholipid to the alkyl substituted diol is typically about 1:1 to about 5:1 and more typically about 1:1 to about 5:2.

The present disclosure is especially useful when the pigment is an untreated or uncoated pigment. For instance, pigments have been modified by various treatment processes with various chemical coatings. If pigments are coated with hydrophobic groups, the treated pigments would be more hydrophobic and thus would be dispersed well in the oil phase of an O/W emulsion. If the pigments are coated with hydrophilic groups would be more hydrophilic and thus would be dispersed well in the water phase of a W/O emulsion. As used herein, untreated pigments are those pigments that have not undergone any coating processes that materially alter their hydrophobic or hydrophilic character. The average particle size or average particle diameter of the pigments is typically less than about 1 µm and more typically greater than about 0.1 µm.

Examples of some pigments employed according to the present disclosure are silica, cerium oxide, zirconium oxide, alumina, calcium carbonate, barium sulphate, calcium sulphate, zinc oxide, iron oxide and titanium dioxide, the composite particles comprising them, and their mixtures. Mention may also be made of laponites, such as, in particular, the products sold by Laporte under the name Laponite XLS, Laponite XLG, Laponite RD and Laponite RDS (these products are sodium magnesium silicates and lithium magnesium sodium silicates). Use may also be made of mixtures of various kinds of pigments. Mention may also be made of colloidal silica/alumina composite particles. The term "silica/alumina composite" is understood to mean silica particles in which aluminum atoms have been partially substituted for silicon atoms, that is to say particles composed of silicon oxide, the surface of which has been modified chemically so as to replace some at least of the silicon atoms by aluminum atoms, forming at most a monomolecular layer of aluminum.

Uncoated or untreated titanium oxide pigments are sold, for example, by the company Tayca under the trade names Microtitanium Dioxide MT 500 B or Microtitanium Dioxide MT 600 B, by the company Degussa under the name P 25, by the company Wackher under the name Transparent titanium oxide PW, by the company Myoshi Kasei under the name UFTR, by the company Tomen under the name ITS and by the company Tioxide under the name Tioveil AQ.

Uncoated or untreated zinc oxide pigments are, for example: those sold under the name Z-Cote by the company Sunsmart; those sold under the name Nanox by the company Elementis; those sold under the name Nanogard WCD 2025 by the company Nanophase Technologies.

Uncoated or untreated cerium oxide pigments are sold under the name Colloidal Cerium Oxide by the company Rhone-Poulenc.

Uncoated or untreated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The pigments are typically employed in amounts of about 0.1% to about 20% and more typically about 1 to about 10% by weight and more typically about 2 to about 8% by weight based upon the total weight of the based upon the total weight of the composition.

The amount of water is typically about 55% to about 80% and more typically about 65 to about 75% by weight based upon the total weight of the composition.

In addition to the water the aqueous phase can also include as diluent hydrophilic compounds, such as, in particular, polyols (polyhydric alcohols), such as, for example, glycerol, propylene glycol, dipropylene glycol and sorbitol, or water-soluble lower alcohols, such as ethanol, isopropanol or butanol. The amount of the hydrophilic diluents can be present in an amount up to about 10% and when present more typically in an amount of about 1 to about 3% by weight based upon the total weight of the composition.

The oily phase contains at least one oil, and especially at least one cosmetic oil. The term "oil" means a fatty substance that is liquid at room temperature (25° C.).

As oils that may be used in the composition of the present disclosure, it is possible to use, for example, hydrocarbon-based oils of animal origin, such as perhydrosqualene (or squalane); hydrocarbon-based oils of plant origin, such as caprylic/capric acid triglycerides, for instance those sold by the company Stearineries Dubois or those sold under the names Miglyol 810, 812 and 818 by the company Dynamit Nobel, or alternatively oils of plant origin, for instance sunflower oil, corn oil, soybean oil, marrow oil, grapeseed oil, sesame seed oil, hazelnut oil, apricot oil, macadamia oil, arara oil, coriander oil, castor oil, avocado oil, jojoba oil and shea butter oil; synthetic oils; silicone oils, for instance volatile or non-volatile polymethylsiloxanes (PDMS) containing a linear or cyclic silicone chain, which are liquid or pasty at room temperature; fluoro oils, such as partially hydrocarbon-based and/or silicone-based fluoro oils, for instance those described in document JP-A-2 295 912; ethers, such as dicaprylyl ether (CTFA name: Dicaprylyl ether); esters, for instance $C_{12}$-$C_{15}$ fatty alkyl benzoates (Finsolv TN from Finetex); arylalkyl benzoates, for instance 2-phenylethyl benzoate (X-Tend 226 from ISP); and amidated oils, for instance isopropyl N-lauroylsarcosinate (Eldew SL-205 from Ajimoto); mixtures thereof.

The oily phase may also comprise one or more fatty substances chosen, for example, from fatty alcohols (cetyl alcohol, stearyl alcohol or cetearyl alcohol), fatty acids (stearic acid) or waxes (paraffin, polyethylene wax, carnauba wax or beeswax). The oily phase may contain lipophilic gelling agents, surfactants or organic or mineral particles.

The amount of oily phase can range, for example, from about 3 to 15% by weight with respect to the total weight of the composition, and more typically about 5 to about 10% by weight, with respect to the total weight of the composition.

The compositions in accordance with the present invention may also comprise standard cosmetic adjuvants chosen especially from fatty substances, organic solvents other than water-miscible volatile organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology.

Hydrophilic thickeners that may be mentioned include carboxyvinyl polymers such as the Carbopol products (carbomers) and the Pemulen products (acrylate/$C_{10}$-$C_{30}$-alkylacrylate copolymer); the methacrylic acid/methyl acrylate/ethoxylated alkyl dimethyl-meta-isopropenyl benzyl isocyanate terpolymer (INCI name: Polyacrylate-3), for instance the product sold by Amerchol under the name Viscophobe DB 1000; polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company Seppic; 2-acrylamido-2-methylpropanesulfonic acid polymers and copolymers, which are optionally crosslinked and/or neutralized, for instance the poly(2-acrylamido-2-methylpropanesulfonic acid) sold by the company Clariant under the trade name Hostacerin AMPS (CTFA name: ammonium polyacryloyldimethyltauramide); cellulose derivatives such as hydroxyethylcellulose; polysaccharides and especially gums such as xanthan gum; and mixtures thereof.

Lipophilic thickeners that may be mentioned include synthetic polymers such as poly ($C_{10}$-$C_{30}$ alkyl acrylates) sold under the name Doresco IPA 13-1 by the company Landec, or modified clays such as hectorite and its derivatives, for instance the products sold under the name Bentone.

Preserving agents that may be mentioned include parahydroxybenzoic acid esters, also known as Parabens® (in particular methyl paraben, ethyl paraben and propyl paraben), phenoxyethanol, formaldehyde generators, for instance imidazolidinylurea or diazolidinylurea, chlorhexidine digluconate, sodium benzoate, iodopropynyl butyl carbamate, alkyltrimethylammonium bromides such as myristyltrimethylammonium bromide (CTFA name: myrtrimonium bromide), dodecyltrimethylammonium bromide, hexadecyltrimethylammonium bromide, and mixtures thereof such as the mixture sold under the name Cetrimide® by the company FEF Chemicals. The preserving agent may be present in the composition according to the invention in a content ranging from 0.001% to 10% by weight, especially ranging from 0.1% to 5% by weight and in particular ranging from 0.2% to 3% by weight relative to the total weight of the composition.

Emulsions according to the present disclosure can be in the form of a liquid, cream, liquid-to-cream, gel, mousse, or compact. Embodiments of the present disclosure exhibit a substantially consistent shade as the composition transitions from the wet to dry state. In other words, the L*a*b* color space coordinates are essentially the same when the composition is wet and when the composition is dry. In embodiments of the present disclosure, the density is about 0.65 to about 1.1 kg/m$^3$ and/or the initial viscosity is about 25 to about 85 UD and preferably about 55 to about 85 UD. The viscosity is measured using a Rheomat R 180 viscometer.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The emulsions of the present disclosure can be prepared by a method which comprises:

1) obtaining a mixture of at least one modified phospholipid and at least one alkyl substituted diol comprising 5 or more carbons in the alkyl chain;
2) obtaining a mixture of water and at least one pigment;
3) combining the mixture of the at least one modified phospholipid and the at least one alkyl substituted diol with the mixture of water and the at least one pigment;
4) obtaining an oil composition; and
5) combining the mixture from 3) with the oil composition of 4) to form a water-in-oil emulsion.

The invention will now be described with reference to the examples that follow, which are given as non-limiting illustrations. In these examples, unless otherwise indicated, the amounts are expressed as weight percentages. The following formulations were prepared; the amounts are indicated as weight percentages. The T0M is the initial viscosity reading of the Rheomat taken at time 0 minutes and the T10M is the viscosity reading of the Rheomat taken at time 10 minutes. A sample is placed under the RheomatR 180 with a Spindle #3 in order to take a measurement (measured in deviated units referred to as UD). L*a*b* color space was measured using a Konica Minolta CR-400 Colorimeter. The instrument settings were: reflectance measurement, 2 degree observer, and C illuminant). Samples of an embodiment of the present invention were measured in both the wet state and as a dried film. The dried film was allowed to dry for 24 hours before measurement. Twelve measurements were taken per sample and averaged together. The significance level was set at p value <0.05. For the L*a*b* system, "L" is an indicator of lightness of the color black (when L*=0) or white (when L*=100). The value "a*" is an indicator of how red (+a*) or green (-a*) the color is. The value "b*" is an indicator of how yellow (+b*) or blue (-b*) the color is.

Example 1

A composition containing about 1.54% by weight of untreated iron oxide and about 2.46% by weight of titanium oxide pigments suspended in the water phase of a water-in-oil emulsion is prepared. The composition has a water content from about 70.4% by weight. The composition comprises about 0.35% by weight of hydrogenated lecithin, and about 0.2% by weight of caprylyl glycol. The composition further contains about 0.2% by weight of disodium ethylene diamine tetraacetic acid (EDTA) active compound; about 0.25% by weight of pentaerthrityl tetra-di-tert butyl hydroxyhydrocinnamate active compound; about 0.15% by weight of citric acid active compound; about 8% by weight of ethylhexyl palmitate; about 1.55% by weight of sodium acrylate/sodium acrylolyldimethyl taurate copolymer, isohexadecane and polysorbate 80; about 0.3% by weight of hydroxyethyl acrylate/sodium acrylolyldimethyl taurate copolymer; about 0.25% by weight of sodium hydroacetate (preservative); about 0.1% by weight of potassium sorbate (preservative; about 0.7% by weight of phenoxyethanol (preservative); about 0.1% by weight of methylthiazolinone (preservative); about 7% by weight of glycerine (auxiliary hydrophilic solvent); about 1% by weight of pentylene glycol (auxiliary hydrophilic solvent); about 2% by weight of silica and titanium dioxide (sun filter); about 0.25% by weight of PEG-30 dihydroxystearate (surfactant); 3% by weight of octyldodecanol and octyldodecyl xyloside (surfactant); about 0.1% by weight of propylene glycol and chamomilla recutita (matricaria flower extract) and about 0.1% by weight of propylene glycol and aloe barbadensis leaf extract. The emulsion is a smooth and even product and is classified as a Western BB cream suitable as a foundation for facial makeup. The initial T0M is 54.6 and T10M is 59.7. The emulsion was completely stable even after 8 weeks. The following results were observed:
  25° C. viscosity: T0M 4 weeks: 31.4
  T10M 4 weeks: 34.65
  40° C. viscosity: TOM 4 weeks: 31.2
  T0M 4 weeks: 28.3.
  The L* is 58.37, a* is 13.43, b* is 22.01, C* is 25.79 and h* is 58.61.

Example 2

A composition containing about 1.54% by weight of untreated iron oxide and about 2.46% by weight of titanium oxide pigments suspended in the water phase of a water-in-oil emulsion is prepared. The composition has a water content from about 68.45% by weight. The composition comprises about 1.5% by weight of hydrogenated lecithin, and about 1% by weight of caprylyl glycol. The composition further contains about 0.2% by weight of disodium ethylene diamine tetraacetic acid (EDTA) active compound; about 0.25% by weight of pentaerthrityl tetra-di-tert butyl hydroxyhydrocinnamate active compound; about 0.15% by weight of citric acid active compound; about 8% by weight of ethylhexyl palmitate; about 1.55% by weight of sodium acrylate/sodium acrylolyldimethyl taurate copolymer, isohexadecane and polysorbate 80; about 0.3% by weight of hydroxyethyl acrylate/sodium acrylolyldimethyl taurate copolymer; about 0.25% by weight of sodium hydroacetate (preservative); about 0.1% by weight of potassium sorbate (preservative; about 0.7% by weight of phenoxyethanol (preservative); about 0.1% by weight of methylthiazolinone (preservative); about 7% by weight of glycerine (auxiliary hydrophilic solvent); about 1% by weight of pentylene glycol (auxiliary hydrophilic solvent); about 2% by weight of silica and titanium dioxide (sun filter); about 0.25% by weight of PEG-30 dihydroxystearate (surfactant); 3% by weight of octyldodecanol and octyldodecyl xyloside (surfactant); about 0.1% by weight of propylene glycol and chamomilla recutita (matricaria flower extract) and about 0.1% by weight of propylene glycol and aloe barbadensis leaf extract.

The emulsion is a smooth and even product and is classified as a Western BB cream suitable as a foundation for facial makeup. Some separation was noted after one week. Accordingly, the higher amounts of lecithin are not as preferred as the lower amounts of up to about 1% by weight based upon the weight of the composition of The initial T0M is 39.1 and T10M is 33.7. The emulsion was stable even after 4 weeks. The following results were observed:
  25° C. viscosity: T0M 24 hours: 30.3
  T10M hours: 33.7
  The L* is 60.02, a* is 12.89, b* is 21.6, C* is 25.25.16 and h* is 59.17.

Example 3

A composition containing about 1.54% by weight of untreated iron oxide pigments and about 2.46% by weight of titanium oxide pigments treated with stearoyl glutamate aluminum hydroxide suspended in the water phase of a water-in-oil emulsion is prepared. The composition has a water content from about 70.4% by weight. The composition comprises about 0.35% by weight of hydrogenated lecithin, and about 0.2% by weight of caprylyl glycol. The composition further contains about 0.2% by weight of disodium ethylene diamine tetraacetic acid (EDTA) (active compound); about 0.25% by weight of pentaerthrityl tetra-di-tert butyl hydroxyhydrocinnamate (active compound); about 0.15% by weight of citric acid (active compound); about 8% by weight of ethylhexyl palmitate; about 1.55% by weight of sodium acrylate/sodium acrylolyldimethyl taurate copolymer, isohexadecane and polysorbate 80; about 0.3% by weight of hydroxyethyl acrylate/sodium acrylolyldimethyl taurate copolymer; about 0.25% by weight of sodium hydroacetate (preservative); about 0.1% by weight of potassium sorbate (preservative; about 0.7% by weight of phenoxyethanol (preservative); about 0.1% by weight of methylthiazolinone (preservative); about 7% by weight of glycerin (auxiliary hydrophilic solvent); about 1% by weight of pentylene glycol (auxiliary hydrophilic solvent); about 2% by weight of silica and titanium dioxide (sun filter); about 0.25% by weight of PEG-30 dihydroxystearate (surfactant); 3% by weight of octyldodecanol and octyldodecyl xyloside (surfactant); about 0.1% by weight of propylene glycol and chamomilla recutita (matricaria flower extract) and about 0.1% by weight of propylene glycol and aloe barbadensis leaf extract.

The emulsion is a smooth and even product and is classified as a Western BB cream suitable as a foundation for facial makeup. There was slight separation at week 8 at about 45° C. and 50° C. The initial T0M is 61.1. The emulsion was stable even after 7 weeks. The following results were observed:

25° C. viscosity: T0M 24 hours: 43.1
T10M 24 hours 48.6
The L* is 59.56, a* is 14.74, b* is 22.1, C* is 26.56 and h* is 56.3.

Example 4

A composition containing about 1.54% by weight of untreated iron oxide and about 2.46% by weight of titanium oxide pigments suspended in the water phase of a water-in-oil emulsion is prepared. The composition has a water content from about 68.45% by weight. The composition comprises about 1.5% by weight of hydrogenated lecithin, and about 0.2% by weight of caprylyl glycol. The composition further contains about 0.2% by weight of disodium ethylene diamine tetraacetic acid (EDTA) active compound; about 0.25% by weight of pentaerthrityl tetra-di-tert butyl hydroxyhydrocinnamate active compound; about 0.15% by weight of citric acid active compound; about 8% by weight of ethylhexyl palmitate; about 1.55% by weight of sodium acrylate/sodium acrylolyldimethyl taurate copolymer, isohexadecane and polysorbate 80; about 0.3% by weight of hydroxyethyl acrylate/sodium acrylolyldimethyl taurate copolymer; about 0.25% by weight of sodium hydroacetate (preservative); about 0.1% by weight of potassium sorbate (preservative; about 0.7% by weight of phenoxyethanol (preservative); about 0.1% by weight of methylthiazolinone (preservative); about 7% by weight of glycerine (auxiliary hydrophilic solvent); about 1% by weight of pentylene glycol (auxiliary hydrophilic solvent); about 2% by weight of silica and titanium dioxide (sun filter); about 0.25% by weight of PEG-30 dihydroxystearate (surfactant); 3% by weight of octyldodecanol and octyldodecyl xyloside (surfactant); about 0.1% by weight of propylene glycol and chamomilla recutita (matricaria flower extract) and about 0.1% by weight of propylene glycol and aloe barbadensis leaf extract.

Comparison Example 1

Water-in-Oil Emulsion with 1,2-Octanediol but without Hydrogenated Lecithin

A composition containing about 1.54% by weight of untreated iron oxide and about 2.46% by weight of titanium oxide pigments suspended in the water phase of a water-in-oil emulsion is prepared. The composition has a water content from about 70.75% by weight. The composition comprises about 0.2% by weight of caprylyl glycol. The composition further contains about 0.2% by weight of disodium ethylene diamine tetraacetic acid (EDTA) active compound; about 0.25% by weight of pentaerthrityl tetra-di-tert butyl hydroxyhydrocinnamate active compound; about 0.15% by weight of citric acid active compound; about 8% by weight of ethylhexyl palmitate; about 1.55% by weight of sodium acrylate/sodium acrylolyldimethyl taurate copolymer, isohexadecane and polysorbate 80; about 0.3% by weight of hydroxyethyl acrylate/sodium acrylolyldimethyl taurate copolymer; about 0.25% by weight of sodium hydroacetate (preservative); about 0.1% by weight of potassium sorbate (preservative; about 0.7% by weight of phenoxyethanol (preservative); about 0.1% by weight of methylthiazolinone (preservative); about 7% by weight of glycerine (auxiliary hydrophilic solvent); about 1% by weight of pentylene glycol (auxiliary hydrophilic solvent); about 2% by weight of silica and titanium dioxide (sun filter); about 0.25% by weight of PEG-30 dihydroxystearate (surfactant); 3% by weight of octyldodecanol and octyldodecyl xyloside (surfactant); about 0.1% by weight of propylene glycol and chamomilla recutita (matricaria flower extract) and about 0.1% by weight of propylene glycol and aloe barbadensis leaf extract.

The composition never looked homogenous and separated. It ran down the spatula when batching.

Comparison Example 2

Water-in-Oil Emulsion with 0.05% of 1,2-Octanediol and 0.05% of Hydrogenated Lecithin A composition containing about 1.54% by weight of untreated iron oxide and about 2.46% by weight of titanium oxide pigments suspended in the water phase of a water-in-oil emulsion is prepared. The composition has a water content from about 70.85% by weight. The composition comprises about 0.05% by weight of hydrogenated lecithin, and about 0.05% by weight of caprylyl glycol. The composition further contains about 0.2% by weight of disodium ethylene diamine tetraacetic acid (EDTA) active compound; about 0.25% by weight of pentaerthrityl tetra-di-tert butyl hydroxyhydrocinnamate active compound; about 0.15% by weight of citric acid active compound; about 8% by weight of ethylhexyl palmitate; about 1.55% by weight of sodium acrylate/sodium acrylolyldimethyl taurate copolymer, isohexadecane and polysorbate 80; about 0.3% by weight of hydroxyethyl acrylate/sodium acrylolyldimethyl taurate copolymer; about 0.25% by weight of sodium hydroacetate (preservative); about 0.1% by weight of potassium sorbate (preservative; about 0.7% by weight of phenoxyethanol (preservative); about 0.1% by weight of methylthiazolinone (preservative); about 7% by weight of glycerine (auxiliary hydrophilic solvent); about 1% by weight of pentylene glycol (auxiliary hydrophilic solvent); about 2% by weight of silica and titanium dioxide (sun filter); about 0.25% by weight of PEG-30 dihydroxystearate (surfactant); 3% by weight of octyldodecanol and octyldodecyl xyloside (surfactant); about 0.1% by weight of propylene glycol and chamomilla recutita (matricaria flower extract) and about 0.1% by weight of propylene glycol and aloe barbadensis leaf extract.

The following results were observed:
Initial viscosity T0M: 21.3; T10M.: 20.7
25° C. viscosity: T0M 24 hours: 22 T10:20.1
The composition lacked adequate viscosity and separated after one week at room temperature.

Exemplary embodiments of the present disclosure include:

Embodiment 1

A composition comprising:
A) an oily phase and
B) an aqueous phase which comprises:
a) water,
b) at least one pigment,
c) at least about 0.1% by weight based upon the weight of the composition of at least one modified phospholipid, and d) at least about 0.1% by weight based upon the weight of the composition of at least one alkyl substituted chain diol comprising 5 or more carbons;

wherein the composition is in the form of an water-in-oil emulsion, and wherein the at least one pigment essentially remains in the water phase.

Embodiment 2

The composition of Embodiment 1, wherein the at least one modified phospholipid is at least one member selected from the group consisting of lecithin and hydrogenated lecithin.

Embodiment 3

The composition of Embodiment 2, wherein the at least one modified phospholipid comprises lecithin.

Embodiment 4

The composition according to any one of Embodiments 1 to 3, wherein the alkyl substituted chain diol is a 5-carbon alkyl chain substituted diol.

Embodiment 5

The composition according to any one of Embodiments 1 to 4, comprising an amount of water of 65 to 80% by weight based upon the total weight of the composition.

Embodiment 6

The composition according to any one of Embodiments 1 to 5, comprising the at least one pigment in an amount of about 0.1 to about 10% by weight, based upon the total weight of the composition.

Embodiment 7

The composition according to any one of Embodiments 1 to 6, wherein the amount of the at least one modified phospholipid is up to about 1% by weight based upon the total weight of the composition; and the amount of the at least one alkyl substituted diol is up to about 1% by weight based upon the total weight of the composition.

Embodiment 8

The composition according to any one of Embodiments 1 to 7, comprising the at least one modified phospholipid in an amount of about 0.2 to about 0.6% by weight based upon the total weight of the composition; and the at least one alkyl substituted diol in an amount of about 0.1 to about 0.3% by weight based upon the total weight of the composition.

Embodiment 9

The composition according to any one of Embodiments 1 to 8, comprising the at least one modified phospholipid in an amount of about 0.2 to about 0.3% by weight based upon the total weight of the composition; and the at least one alkyl substituted diol in an amount of about 0.2 to about 0.3% by weight based upon the total weight of the composition.

Embodiment 10

The composition according to any one of Embodiments 1 to 9, wherein the weight ratio of the at least one modified phospholipid to the alkyl diol is about 1:1 to about 5:1.

Embodiment 11

The composition according to any one of Embodiments 1 to 10, wherein the weight ratio of the at least one modified phospholipid to the alkyl diol is about 1:1 to about 5:2.

Embodiment 12

The composition of according to any one of Embodiments 1 to 11, wherein the at least one pigment is an untreated pigment.

Embodiment 13

The composition according to any one of Embodiments 1 to 12, wherein the L*a*b* color space coordinates are essentially the same when the composition is wet and when the composition is dry.

Embodiment 14

A cosmetic comprising the composition according to any one of Embodiments 1 to 13, wherein the cosmetic is in the form of a liquid, cream, liquid-to-cream, gel, mousse, or compact.

Embodiment 15

The cosmetic according to any one of Embodiments 1 to 14, wherein the density of the cosmetic is about 0.65 to about 1.1 kg/m$^3$.

Embodiment 16

The cosmetic according to any one of Embodiments 1 to 15, wherein the viscosity of the cosmetic is about 25 to about 85 UD.

Embodiment 17

The cosmetic according to any one of Embodiments 1 to 15, wherein the viscosity of the cosmetic is about 55 to about 85 UD.

Embodiment 18

The cosmetic according to any one of Embodiments 1 to 17, wherein the L*a*b* color space coordinates are essentially the same when the cosmetic is wet and when the cosmetic is dry.

Embodiment 19

The composition according to any one of Embodiments 1 to 18, which remains stable for at least 8 weeks at room temperature.

Embodiment 20

The composition according to any one of Embodiments 1 to 19, further comprising additional components selected from the group consisting of active compounds, preservatives, solvents, sun filters, surfactants, vegetables extracts, and mixtures thereof.

Embodiment 21

A process for the cosmetic treatment of a keratinous substance, comprising applying the composition according to any one of Embodiments 1 to 20 to the keratinous substance.

Embodiment 22

A method of producing the composition according to any one of Embodiments 1 to 20, comprising:
1) obtaining a mixture of at least one modified phospholipid and at least one alkyl substituted diol comprising 5 or more carbons in the alkyl chain;
2) obtaining a mixture of water and at least one pigment;
3) combining the mixture of the at least one modified phospholipids and the at least one alkyl substituted diol with the mixture of the at least one pigment and water;
4) obtaining an oil composition; and
5) combining the mixture from 3) with the oil composition of 4) to form an water-in-oil emulsion.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The term "at least one", as used herein, means one or more, and thus the term includes individual components as well as mixtures or combinations.

The composition and methods of the present invention can comprise, consist of, or consist essentially of the essential elements and limitations of the invention described herein, as well as any additional or optional ingredients, components, or limitations described herein or otherwise useful ingredients found in cosmetic compositions.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

What is claimed is:

1. A composition comprising:
A) an oily phase and
B) an aqueous phase which comprises:
a) water,
b) at least one pigment,
c) at least about 0.1% by weight based upon the weight of the composition of at least one modified phospholipid, and
d) at least about 0.1% by weight based upon the weight of the composition of at least one alkyl substituted chain diol comprising 5 or more carbons;
wherein the composition is in the form of an water-in-oil emulsion, and
wherein the at least one pigment essentially remains in the water phase.

2. The composition of claim 1, wherein the at least one modified phospholipid is at least one member selected from the group consisting of lecithin and hydrogenated lecithin.

3. The composition of claim 2, wherein the at least one modified phospholipid comprises lecithin.

4. The composition of claim 1, wherein the alkyl substituted chain diol is a 5-carbon alkyl chain substituted diol.

5. The composition of claim 1, comprising an amount of water of 65 to 80% by weight based upon the total weight of the composition.

6. The composition of claim 1, comprising the at least one pigment in an amount of about 0.1 to about 10% by weight, based upon the total weight of the composition.

7. The composition of claim 1, wherein the amount of the at least one modified phospholipid is up to about 1% by weight based upon the total weight of the composition; and the amount of the at least one alkyl substituted diol is up to about 1% by weight based upon the total weight of the composition.

8. The composition of claim 1, comprising the at least one modified phospholipid in an amount of about 0.2 to about 0.6% by weight based upon the total weight of the composition; and the at least one alkyl substituted diol in an amount of about 0.1 to about 0.3% by weight based upon the total weight of the composition.

9. The composition of claim 1, comprising the at least one modified phospholipid in an amount of about 0.2 to about 0.3% by weight based upon the total weight of the composition; and the at least one alkyl substituted diol in an amount of about 0.2 to about 0.3% by weight based upon the total weight of the composition.

10. The composition of claim 1, wherein the weight ratio of the at least one modified phospholipid to the alkyl diol is about 1:1 to about 5:1.

11. The composition of claim 1, wherein the weight ratio of the at least one modified phospholipid to the alkyl diol is about 1:1 to about 5:2.

12. The composition of claim 1, wherein the at least one pigment is an untreated pigment.

13. The composition of claim 1, wherein the L*a*b* color space coordinates are essentially the same when the composition is wet and when the composition is dry.

14. A cosmetic comprising the composition of claim 1, wherein the cosmetic is in the form of a liquid, cream, liquid-to-cream, gel, mousse, or compact.

15. The cosmetic of claim 14, wherein the density of the cosmetic is about 0.65 to about 1.1 kg/m$^3$.

16. The cosmetic of claim 14, wherein the viscosity of the cosmetic is about 25 to about 85 UD.

17. The cosmetic of claim 14, wherein the viscosity of the cosmetic is about 55 to about 85 UD.

18. The cosmetic of claim 14, wherein the L*a*b* color space coordinates are essentially the same when the cosmetic is wet and when the cosmetic is dry.

19. The composition of claim 1, which remains stable for at least 8 weeks at room temperature.

20. The composition of claim 1, further comprising additional components selected from the group consisting of active compounds, preservatives, solvents, sun filters, surfactants, vegetables extracts, and mixtures thereof.

21. A process for the cosmetic treatment of a keratinous substance, comprising applying the composition of claim 1 to the keratinous substance.

22. A method of producing the composition of claim 1, comprising:
   1) obtaining a mixture of at least one modified phospholipid and at least one alkyl substituted diol comprising 5 or more carbons in the alkyl chain;
   2) obtaining a mixture of water and at least one pigment;
   3) combining the mixture of the at least one modified phospholipids and the at least one alkyl substituted diol with the mixture of the at least one pigment and water;
   4) obtaining an oil composition; and
   5) combining the mixture from 3) with the oil composition of 4) to form an water-in-oil emulsion.

* * * * *